United States Patent [19]
Sarvazyan et al.

[11] Patent Number: 5,810,731
[45] Date of Patent: *Sep. 22, 1998

[54] METHOD AND APPARATUS FOR ELASTICITY IMAGING USING REMOTELY INDUCED SHEAR WAVE

[75] Inventors: Armen P. Sarvazyan, East Brunswick, N.J.; Oleg V. Rudenko, Moscow, Russian Federation

[73] Assignee: Artann Laboratories, East Brunswick, N.J.

[*] Notice: The term of this patent shall not extend beyond the expiration date of Pat. No. 5,606,971.

[21] Appl. No.: 812,937

[22] Filed: Mar. 4, 1997

Related U.S. Application Data

[63] Continuation-in-part of Ser. No. 555,851, Nov. 13, 1995, Pat. No. 5,606,971.

[51] Int. Cl.$^6$ ..................................................... A61B 8/00
[52] U.S. Cl. ............................................................ 600/438
[58] Field of Search ................................ 600/438, 587, 600/444; 73/597, 602

[56] References Cited

U.S. PATENT DOCUMENTS

| | | | |
|---|---|---|---|
| 4,947,851 | 8/1990 | Sarvazyan et al. | 600/438 |
| 5,038,787 | 8/1991 | Antich et al. | 600/437 |
| 5,099,848 | 3/1992 | Parker et al. | 128/661.07 |
| 5,107,837 | 4/1992 | Ophir et al. | 128/660.01 |
| 5,115,808 | 5/1992 | Popovic et al. | 600/438 |
| 5,293,870 | 3/1994 | Ophir et al. | 128/660.01 |

OTHER PUBLICATIONS

T.A. Krouskop et al., *A Pulsed Doppler Ultrasonic System for Making Non–Invasive Measurement of Mechanical Properties of Soft Tissue* (1987) 24 J. Rehab. Res. Dev., vol. 24, No. 2 pp. 1–8.

*Sonoelasticity Images Derived From Ultrasound Signals In Mechanically Vibrated Tissues,* (1990) Ultrasound in Med. & Biol. vol. 16, No. 3, pp. 231–239.

Yamakoshi et al., *Ultrasonic Imaging of Internal Vibration of Soft Tissue Under Forced Vibration* (1990), IEEE Transactions on Ultrasonics, Ferroelectric, and Frequency Control, vol. 7(2), pp. 45–53.

M. O'Donnell et al., *Internal Dosplacement And Strain Imaging Using Ultronic Speckle Tracking,* IEEE Trans. on Ultrasonic Ferroelectrics and Frequency Control; vol. 41, 314–325, (1994).

R. Muthupillai et al., *Magnetic Resonance Elastography by Direct Visualization of Propagating Acoustic Strain Waves,* (1995) Science, vol. 269, pp. 1854–1857.

*An Experimental Investigation of Streaming in Pulsed Diagnotic Ultrasound Beams* (1989) Ultrasound Med Biol. vol. 15, pp. 363–373.

O.V. Rudenko et al. *High–Power Acoustic Beams: Self–Action of Discontinuous Waves, Focusing of Pulses, and Extracorporeal Lithotripsy* (1991) Moscow University Physics Bulletin, vol. 46, No. 1, pp. 5–18.

(List continued on next page.)

*Primary Examiner*—George Manuel
*Attorney, Agent, or Firm*—Mathews, Collins, Shepherd & Gould, P.A.

[57] ABSTRACT

A method and devices for Shear Wave Elasticity Imaging (SWEI). The method employs a focused acoustic pulse which remotely induces a shear wave in tissue. The values of the shear modulus and dynamic shear viscosity of tissue are evaluated from the values of propagation parameters of shear acoustic waves detected by various means including Doppler ultrasound and Magnetic Resonance Imaging. Several devices for carrying out the method are described. Devices based on the method can be used as a diagnostic tool in the detection of abnormalities in tissue, such as those caused by cancer or other lesions and characterizing processes in tissues accompanied by changes in their mechanical properties. The devices can also be used for assessment of brain tissue and evaluation of the biomechanical state of muscle.

23 Claims, 10 Drawing Sheets

OTHER PUBLICATIONS

A.P. Sarvazyan et al. *Biophysical Bases of Elasticity Imaging*, Acoustic Imaging, vol. 21, (1995), Ed. J.P. Jones, Plenum Press, NY 223–240.

J.B. Fowlkes et al.*Magnetic–Resonance Imaging Techniques For Detection Of Elasticity Variation*, (1995) Med. Phys. vol. 22, pp. 1771–1778.

O.V. Rudenko et al*Acoustic Radiation Force And Streaming Induced By Focused Nonlinear Ultrasound* (1996) JASA, vol. 99, No. 5, pp. 91–98.

V. Andreev et al. *Excitation of Shear Wave Within The Thickness Of Rubber–Like Material By Focused Longitudinal Wave* (1996) Nonlinear Acoustics in Perspective, 14th International Symposium of Nonlinear Acoustics, Nanjing Univ. Press. pp. 456–462.

Jean–Louis Thomas et al.*Ultrasonic Beam Focusing Through Tissue Inhomogeneities With A Time Reversal Mirror: Application To Transskull Therapy*, (1996) IEEE Trans. on Ultrasonics, Ferroelectrics, and Frequency Control, vol. 43, No. 6, pp. 1122–1129.

METHOD AND APPARATUS FOR ELASTICITY IMAGING USING REMOTELY INDUCED SHEAR WAVE

CROSS-REFERENCE TO RELATED APPLICATION

This application is a continuation-in-part of Ser. No. 08/555,851, entitled "Method and Device for Shear Wave Elasticity Imaging" filed Nov. 13, 1995, now U.S. Pat. No. 5,606,971, hereby incorporated by reference into this application.

BACKGROUND OF THE INVENTION

1. Field of the Invention

The present invention relates to a method and devices for determining tissue elasticity in various parts of the body and using such information as a diagnostic tool in the detection of abnormalities of tissue, such as those caused by cancer or other lesions and characterizing processes in tissues accompanied by changes in their mechanical properties, such as muscle contraction, development of edema in brain, etc. The clinical importance and the diagnostic value of elasticity imaging of tissues is based on the observation that changes of shear elasticity modulus of tissues reach several orders-of-magnitude during pathological and physiological processes in the body.

2. Description of the Related Art

There are number of methods of elasticity imaging where elasticity of tissues is evaluated using the data on the strain in a tissue subjected to a given stress. In most of these methods, the information about the strain in the tissue is obtained with the use of conventional ultrasonic imaging techniques.

One approach attempts to determine the shear elasticity of tissue by applying a low frequency vibration (e.g. 100 Hz) to the tissue surface while measuring the amplitude and phase of tissue vibration using ultrasound imaging techniques. See e.g., T. A. Krouskop et al., *A Pulsed Doppler Ultrasonic System for Making Non-Invasive Measurement of Mechanical Properties of Soft Tissue*, J. Rehab. Res. Dev. Vol. 24, 1–8 (1987); see also R. M. Lerner et al., *"Sonoelasticity" Images Derived from Ultrasound Signals in Mechanically Vibrated Tissues*, Ultrasound in Med. & Biol. Vol. 16, No. 3, 231–239 (1990), and K. J. Parker et al., U.S. Pat. No. 5,099,848 (1992), and Y. Yamakoshi et al., *Ultrasonic Imaging of Internal Vibration of Soft Tissue Under Forced Vibration*, IEEE Transactions on Ultrasonics, Ferroelectrics, and Frequency Control, Vol. 7, No. 2, 45–53 (1990).

A method for measuring and imaging tissue elasticity is described in Ophir et al., U.S. Pat. No. 5,107,837 (1992), and Ophir et al., U.S. Pat. No. 5,293,870 (1994). This method includes emitting ultrasonic waves along a path into the tissue and detecting an echo sequence resulting from the ultrasonic wave pulse. The tissue is then compressed (or alternatively uncompressed from a compressed state) along the path and during such compressing, a second pulse of ultrasonic waves is sent along the path into the tissue. The second echo sequence resulting from the second ultrasonic wave pulse is detected and then the differential displacement of selected echo segments of the first and second echo sequences are measured. A selected echo segment of the echo sequence, i.e., reflected RF signal, corresponds to a particular echo source within the tissue along the beam axis of the transducer. Time shifts in the echo segment are examined to measure compressibilities of the tissue regions.

More recently, M. O'Donnell et al., *Internal Displacement And Strain Imaging Using Ultrasonic Speckle Tracking*. IEEE Transactions on Ultrasonic Ferroelectrics and Frequency Control; Vol. 41, 314–325, (1994) have used Fourier based speckle tracking techniques to improve the strain measurements in the tissue produced by an external mechanical load. It has been shown that by applying incremental deformations and collecting large set of complex B-Scan images, the strain signal-to-noise ratio can be significantly improved.

The various approaches differ both in how the medium is stressed and in how the resulting strain is measured. The use of MRI for detection of shear waves in soft tissue induced by a mechanical actuator attached to the surface of the tissue is described in R. Muthupillai et al., *Magnetic Resonance Elastography By Direct Visualization Of Propagating Acoustic Strain Waves*, Science vol., 269, 1854–1857 (1995). T. Sugimoto et al., *Tissue Hardness Measurement Using The Radiation Force of Focused Ultrasound*. IEEE 1990 Ultrasonic Symposium, 1377–80 (1990) suggested a measurement technique of hardness, where the radiation force of focused ultrasound was used to generate the deformation of the tissue, and deformation was measured as a function of time by a conventional pulse-echo technique. The radiation pressure of focused ultrasound exerts such a substantial mechanical stress in the media that even at the exposure levels typical for medical ultrasonic pulse-echo imaging devices significant acoustical streaming can be induced in a liquid. See H. C. Starritt et al., *An Experimental Investigation of Streaming in Pulsed Diagnostic Ultrasound Beams*. Ultrasound Med Biol; Vol. 15, 363–373 (1989).

The use of radiation pressure of focused ultrasound to exert force in medium to obtain information on its mechanical properties has been described. See S. Dymling et al., *Acoustic Method For Measuring Properties of a Mobile Medium*. U.S. Pat. No. 5,056,357 (1991). They derived the information on the viscosity of the fluids by measuring the velocity of the streaming induced by radiation pressure using Doppler ultrasound.

Other types of acoustic pulses have been applied to tissue for various medical applications. For example, single monopolar videopulses are used in extracorporeal lithotripsy for kidney stones destruction and other bioconcrement fragmentation in the human body (See e.g., O. V. Rudenko and O. A. Sapozhnikov, *High-power Acoustic Beams: Self-action of Discontinuous Waves, Focusing of Pulses, and Extracorporeal Lithotripsy*, Moscow University Physics Bulletin, Vol. 46, No. 1, 5–18, Allerton Press, Inc. (1991). These acoustic single video pulses can be generated by different methods, such as, for example, by electrohydraulic and optoacoustic source. (See e.g., O. V. Rudenko and O. A. Sapozhnikov, *High-power Acoustic Beams: Self-action of Discontinuous Waves, Focusing of Pulses, and Extracorporeal Lithotripsy*, Moscow University Physics Bulletin, Vol. 46, No. 1, 5–18, Allerton Press, Inc. (1991). In the commercially available lithotripters manufactured by Dornier Corporation, Germany, electrohydraulic source of acoustic pulse is used. An acoustic pulse is generated by electric spark in water. The high-voltage energy produces electric discharge, and a spark arises between electrodes immersed in a coupling liquid. The electrodes are positioned at the first focus of elliptic reflector so that generated acoustic pulse in a form of a shock wave is focused in the tissue at the second focus of the reflector. The optoacoustic method is based on transformation of light energy into mechanical energy. The pulsed laser source radiates the light pulse acting on optoacoustic cell containing absorbing focusing layer. Thermal expansion of the layer excites in the coupling liquid high-power short acoustic pulse upon absorption of modulated optical radiation in the medium.

In the conventional methods of elasticity imaging, static or oscillatory deformation of the tissue is produced by a deformation means applied directly to the accessible surface of tissue (See e.g. Parker et al., U.S. Pat. No. 5,099,848 (1992), Y. Yamakoshi et al., *Ultrasonic Imaging of Internal Vibration of Soft Tissue Under Forced Vibration*, IEEE Transactions on Ultrasonics, Ferroelectrics, and Frequency Control, Vol. 7, No. 2, 45–53 (1990), Ophir et al., U.S. Pat. No. 5,107,837 (1992), and Ophir et al., U.S. Pat. No. 5,293,870 (1994)). These methods have the drawback that they require direct contact with the imaged tissue and can not be used for imaging if there is no mechanically accessible surface of the tissue, such as in the case of the brain which is surrounded by an intact skull.

Conventional techniques for evaluating viscoelastic properties in muscle have been mainly limited to qualitative and subjective method of palpation. Existing data are very scarce and fragmentary. There have been many attempts to develop methods and devices to quantify palpation of muscle using indentation test, which is a direct measurement of relation between an applied deforming force and the depth of penetration of a rigid indenter into muscle tissue. This approach has the drawback of being a static procedure and cannot be used for continuous monitoring in the course of motion.

SUMMARY OF THE INVENTION

The present invention relates to a method and devices for Shear Wave Elasticity Imaging (SWEI) in which the shear strain is induced remotely in the tissue in the form of highly attenuating shear waves.

The core of this method is shear wave generation by radiation force of a focused acoustic source, such as focused ultrasound transducer or a source of a single monopolar acoustic pulse. These remotely induced waves are detected and the tissue viscoelastic properties are evaluated from the measured propagation speed and attenuation of the shear waves.

The values of the shear modulus G and dynamic shear viscosity $\eta$ of tissue are evaluated from the measured values of velocity $C_t$ and attenuation $\alpha_s$ of shear waves using the equations $$G = \frac{(R^2 - X^2)}{\rho}, \quad \eta = \frac{2RX}{\omega\rho}, \quad C_t = \frac{R^2 + X^2 2}{\rho R}, \quad \text{and } \alpha = \frac{\rho\omega X}{(R^2 + X^2)},$$

where R and X are real and imaginary components of acoustic impedance of tissue, $\rho$ is the density of the material, and $\omega$ is the angular frequency. (See L. A. Frizzell, E. L. Carstensen, and J. F. Dyro, *Shear Properties of Mammalian Tissue at Low Megahertz Frequencies*, J. Acoust. Soc. Am., Vol. 60, No. 6, 1409–1411, (1977).) There are different possibilities of ultrasonically deriving propagation parameters of shear waves needed for evaluation of tissue viscoelastic properties.

Preferably, the focused acoustic wave is a single acoustic pulse with a duration in the range of $10^{-2}$ to $10^{-9}$ seconds. An advantage of using short monopolar acoustic pulses for remote shear wave generation is an increase in the radiation force as compared with an ultrasonic pulse of the same energy. The focused energy used to induce shear waves in tissue can be, for example, an amplitude modulated ultrasound optoacoustic or electrohydraulic. For particular applications, such as the breast, an interrogating pulse can be transmitted from the side opposite the focused acoustic pulse. A detection system determines at least one of the shear wave propagation parameters such as shear wave velocity, shear waves attenuation coefficient, amplitude and velocity of shear displacement of tissue particles in the propagating shear wave, spatial and temporal dependencies of these amplitude and velocity of shear displacement of tissue particles. The shear wave can be detected with a magnetic resonance imaging device or an interrogating ultrasonic transducer. Alternatively, electromagnetic waves induced by the shear motion of the tissue at the focal region can be detected.

SWEI can be used for assessment of brain tissue. Preferably, a SWEI device transmits a pulse through the temporal bone of an intact skull to generate a shear wave in the brain tissue. In addition, SWEI can be used for evaluation of the biomechanical state of muscle. Detection of shear wave propagation parameters in the muscle provide data related to muscle physiological activity and pathology.

DETAILED DESCRIPTION OF THE INVENTION

Figure 1:
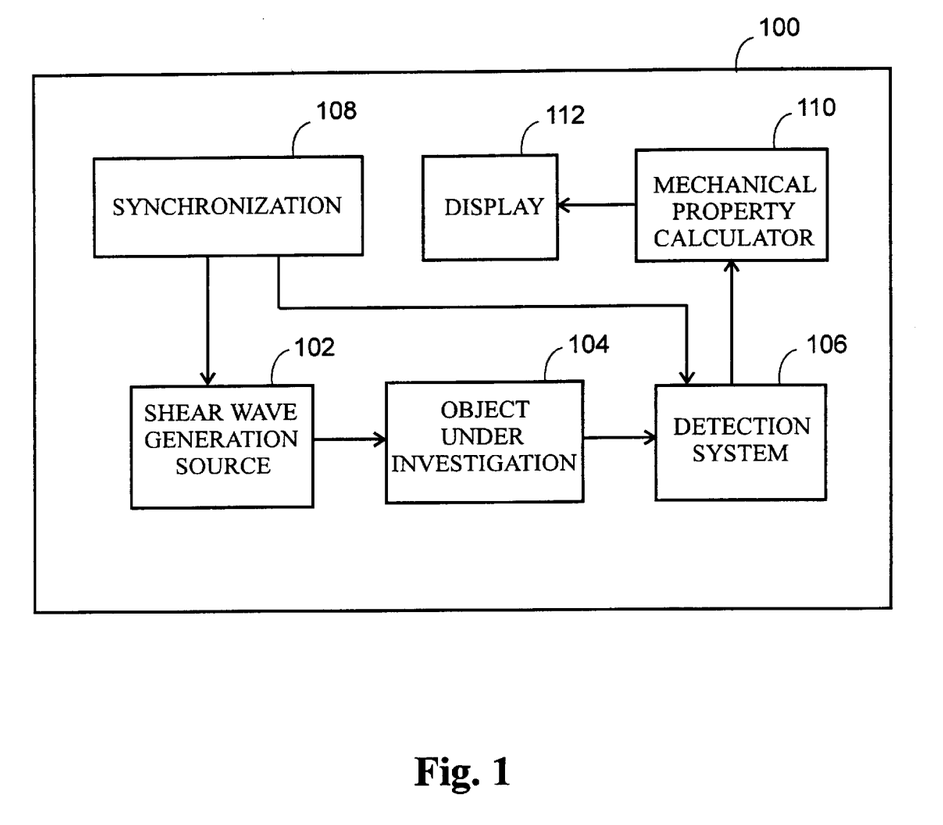
FIG. 1 shows a general schematic of the method and the device.

FIG. 1 shows a schematic of an embodiment of the present invention in a general form, to explain a basic principle of he operation of the device and method which can be applied and other possible embodiments. The complete system designated by the numeral 100, comprises an external source of focused energy 102 that remotely generates shear waves in the investigated tissue 104. The focused energy used to induce shear waves in the tissue can be amplitude modulated ultrasound but other types of focused acoustic energy sources, such as optoacoustic and electro-hydraulic sources, can be used. The detection system 106 determines at least one of the shear wave propagation parameters such as shear wave velocity, shear wave attenuation coefficient, amplitude and velocity of shear displacement of tissue particles in the propagating shear wave, spatial and temporal dependencies of these amplitude and velocity of shear displacement of tissue particles. The functioning of shear wave generation source 102 and the detection system 106 usually need to be coordinated in time by a timing or synchronization element 108. Using the obtained data on at least one propagation parameter of shear waves the mechanical property calculator 110 evaluates at least one of the mechanical properties or tissue such as shear elasticity modulus, Young's modulus, dynamic shear viscosity, and mechanical impedance of the tissue. The calculated mechanical parameter is displayed on a display 112. The detection system 106 can employ direct detection of shear waves on the surface of the tissue, or indirect remote detection of shear waves inside the tissue using different forms of radiation, as it is described in FIG. 2. Remote indirect detection of shear waves can be achieved not only with ultrasound but also using other types of energy such as electromagnetic waves and imaging techniques such as MRI. The use of MRI for detection of tissue motion in evaluating tissue elasticity is described in A. P. Sarvazyan et al. *Biophysical Bases of Elasticity Imaging*, in: Acoustic Imaging, Vol. 21, Ed. J. P. Jones, Plenum Press, New York, 223–240 (1995) and R. Multupillair et al, *Magnetic Resonance Elastography by Direct Visualization of Progagating Acoustic Strain Waves*. Science Vol. 269, 1854–1857 (1995).

Figure 2:
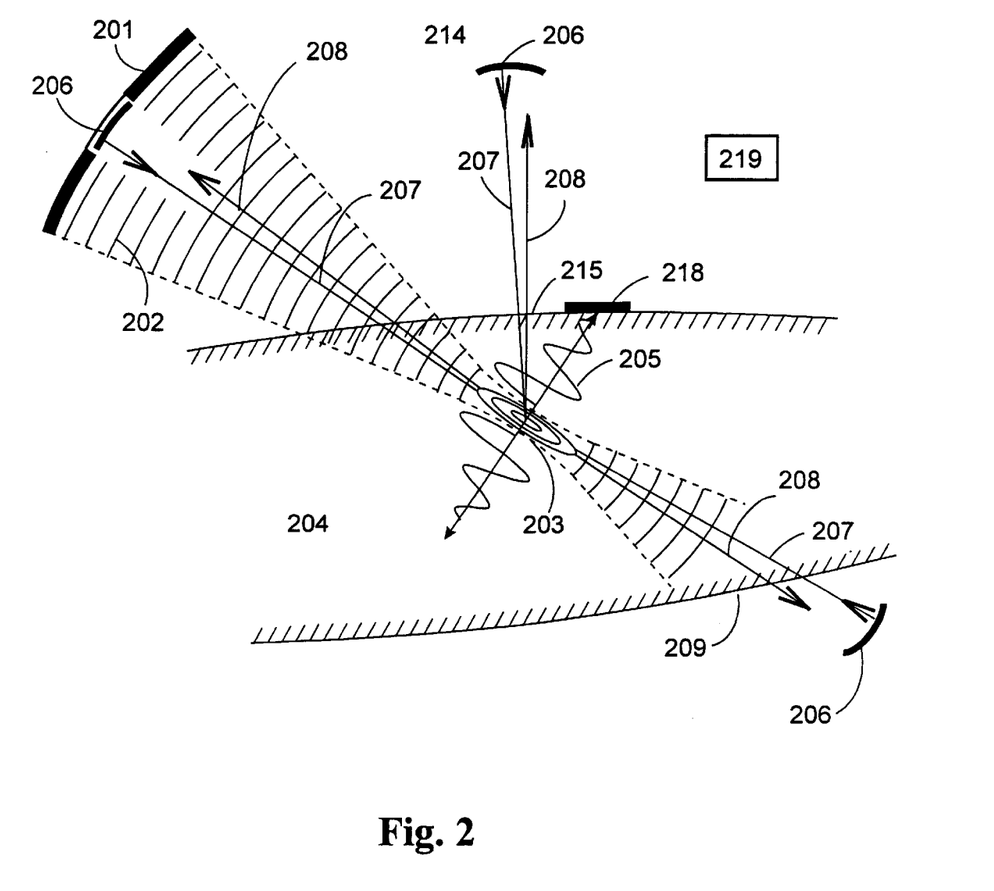
FIG. 2 shows a schematic diagram of different possible ways of acoustic detection of remotely induced shear wave propagation parameters.

Various possibilities of detection of a remotely induced shear wave in the present method and apparatus for elasticity imaging are shown in FIG. 2. Source for focused acoustic pulse 201 generates a pulse 202 to focal region 203 of tissue 204. Preferably, source for focused acoustic pulse 201 generates short acoustic pulses having a duration in the range of $10^{-2}$ to $10^{-7}$s. Source for focused acoustic pulse pulse 201 can generate focused monopolar acoustic pulses with conventional methods such as, for example, electrohydraulic, opto acoustic, electromagnetic and piezoelectric. The range of the pulse duration is limited by the following phenomena. The longer the pulse is, the stronger is the impact of diffraction and it becomes more and more difficult to focus the pulse in a small region of the tissue. The shorter the pulse is, the higher is the absorption of acoustic wave in the tissue and the wave may attenuate before it reaches the focal region.

An advantage of using short monopolar acoustic pulses for remote shear wave generation is an increase in the radiation force as compared with an ultrasonic pulse of the same energy. This gain is due to a radically different dependency of radiation force on acoustic wave amplitude for the monopolar acoustic pulse than for an amplitude modulated ultrasonic pulse. (See e.g. O. V. Rudenko and O. A. Sapozhnikov, *High-power Acoustic Beams: Self-Action Of Discontinuous Waves, Focusing Of Pulses, And Extra-cornoreal Lithotripsy*, Moscow University Physics Bulletin, Vol. 46, No. 1, 5–18, Allerton Press, Inc. (1991).

It is contemplated that the propagation parameters of the shear waves induced by the radiation pressure of the amplitude modulated focused ultrasound can be detected remotely using an ultrasonic pulse-echo imaging technique. The shear waves and the resulting shear strain are detected by ultrasound interrogation involving cross-correlation of sequential image data. The ultrasonic wave backscattered from the focal region of the excitation transducer contains information on the parameters of the shear waves. Since the excitation and interrogation ultrasonic waves are of the same frequency range, the same focused transducer or an array can be used for both functions: to induce shear wave and to measure its propagation properties. The modes of remote ultrasonic detection of shear waves may also include pulsed and continuous Doppler techniques. Imaging ultrasonic transducer 206 transmits on interrogating pulse 207 to focal region 203. Reflected ultrasonic pulse 208 containing information of shear wave parameters is received at imaging ultrasonic transducer 206.

In particular applications, for example, when tissue 204 is the breast, interrogating pulse 207 can be transmitted from opposite side 209 from source for focused acoustic pulse 201. Alternatively, parameters of the shear wave 205 can be detected with imaging untrasonic transducer 206 at various positions, such as position 215. Shear wave 205 can be detected with a low frequency shear wave detector 218.

Focused acoustic pulse source 214 can generate focused monopolar acoustic pulses with conventional methods such as, for example, electrohydraulic, opto acoustic, electromagnetic and piezoelectric. (See e.g., O. V. Rudenko and O. A. Sapozhnikov, *High-power acoustic beams: self-action of discontinuous waves, focusing of pulses, and extracornoreal lithotripsy*, Moscow University Physics Bulletin, Vol. 46, No. 1, 5–18, Allerton Press, Inc. (1991).

Alternatively, shear waves 205 can be detected a device 218 using with other imaging techniques, such as Magnetic Resonance Imaging and electromagnetic waves. MRI is capable of detecting shear deformation of soft tissue (see e.g., Fowlkes JB et al., *Magnetic Resonance Imaging Techniques for Detection of Elasticity Variation*, Medical Physics, Vol. 22, 1771–1778, (1995). Shear wave propagation parameters, such as shear viscosity η, shear elasticity modulus G, Young's modulus and shear displacement of tissue particles can be determined from MRI detection. The electromagnetic waves that are induced by the shear motion of the tissue at the focal region 203 can be used to detect this shear motion.

The equations that enable analytical investigation of dependencies of radiation pressure and resulting shear motion on the parameters of the acoustic field and medium are derived in: O. V. Rudenko, A. P. Sarvazyan and S. V. Emelianov, *Acoustic radiation force and streaming induced by focused nonlinear ultrasound*, JASA, v.99, No 5, 91–98 (1996), and also in Andreev et al., *Excitation of Shear Wave within the thickness of rubber-like material by focused longitudinal wave*, pp. 457–462, Nonlinear Acoustics in Perspective, Proceedings of 14th International Symposium on Nonlinear Acoustics, Ed. R. J. Wei, Nanjing University Press (1996).

Low frequency shear oscillations induced in the tissue by the radiation force of an acoustic pulse are described by the equation:

$$\frac{\partial^2 s_x}{\partial t^2} - \left( c_t^2 + \nu \frac{\partial}{\partial t} \right) \Delta_\perp s_x = F_x,$$

where $F_x$ is component of the force acting along the beam direction and $$c_t = \sqrt{\frac{G}{\rho}}$$

is a speed of the shear waves propagation, $v=\mu/\rho$ is a kinematic shear viscosity, and $s_x$ is a component of the displacement vector along the x direction.

The results of calculations of the axial displacement $s_x$ in the focal plane, i.e., perpendicular to the beam axis plane at the geometrical focus of the transducer for the 100 μsec long rectangular acoustic pulse and the shear wave speed $c_t$ equal to 2 m/sec are presented in FIGS. 3A–3H.

Figure 3A:
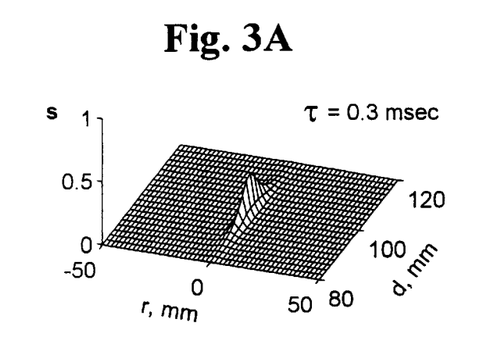
FIG. 3A illustrates a plot of a shear wave pattern at time 0.3 msec from transmission.
Figure 3B:
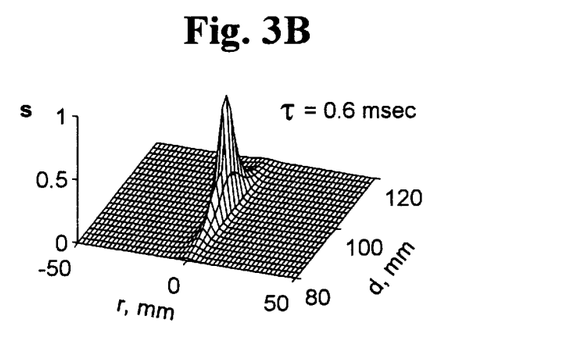
FIG. 3B illustrates a plot of a shear wave pattern at time 0.6 msec from transmission.
Figure 3C:
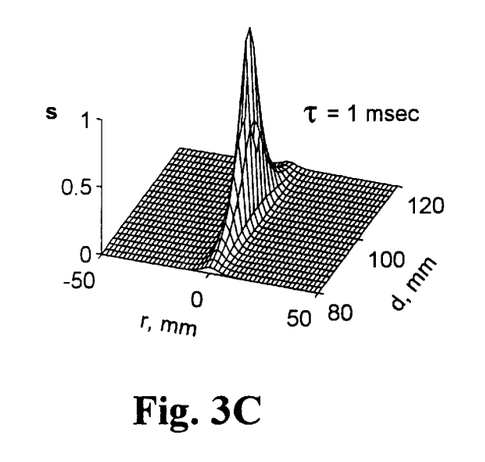
FIG. 3C illustrates a plot of a shear wave pattern at time 1.0 msec from transmission.
Figure 3D:
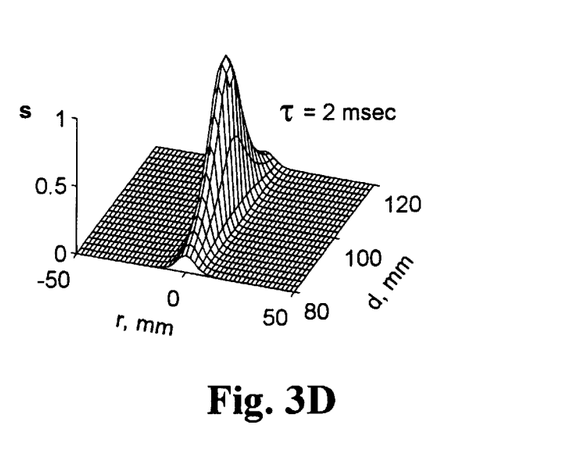
FIG. 3D illustrates a plot of a shear wave pattern at time 2.0 msec from is transmission.
Figure 3E:
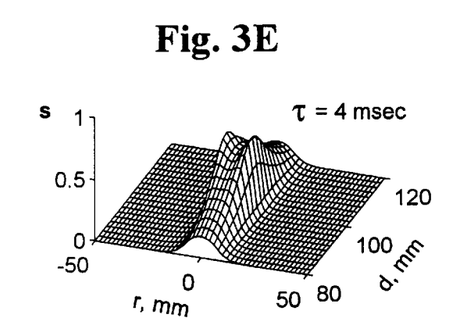
FIG. 3E illustrates a plot of shear wave pattern at time 4.0 msec from transmission.
Figure 3F:
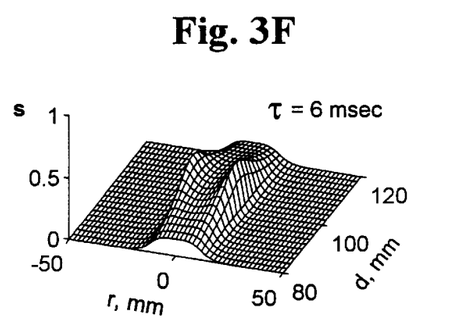
FIG. 3F illustrates a plot of shear wave pattern at time 6.0 msec from transmission.
Figure 3G:
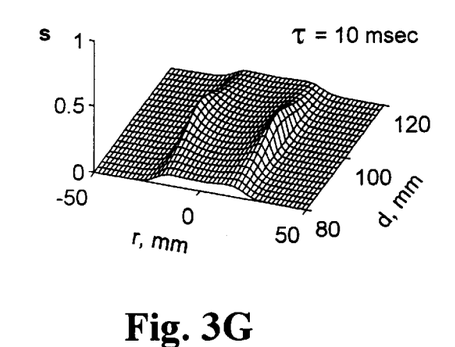
FIG. 3G illustrates a plot of shear wave pattern at time 10.0 msec from transmission.
Figure 3H:
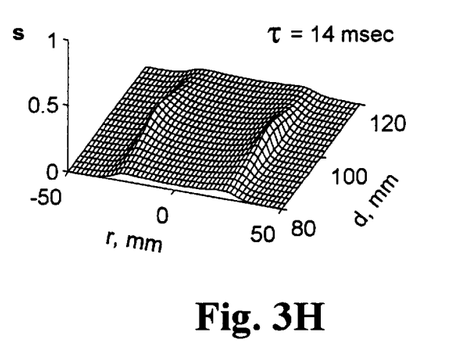
FIG. 3H illustrates a plot of shear wave pattern at time 14.0 msec from transmission.

Initially, the shear displacement magnitude along the beam axis increasing in time (FIGS. 3A, 3B, and 3C). This increase continues due to inertia for some time after acoustical pulse is terminated. The displacement reaches the maximum at the time $\tau_{max}$ needed for the shear wave to travel the distance equal to the radius a of the focal region: $\tau_{max}=a/c_t$. Having in mind that $$c_t = \sqrt{\frac{G}{\rho}},$$

we obtain that at the first approximation $G=\rho(a/\tau_{max})^2$ is obtained. After reaching the maximum, the displacement starts to decrease due the absorption of the shear waves as well as due to the formation of the diverging cylindrical wave propagating away from the axis (FIGS. 3D, 3E, 3F, 3G, and 3H). At that stage, the distance between the wave front and axis of the beam linearly increases as $\tau \cdot c_t$.

Figure 4:
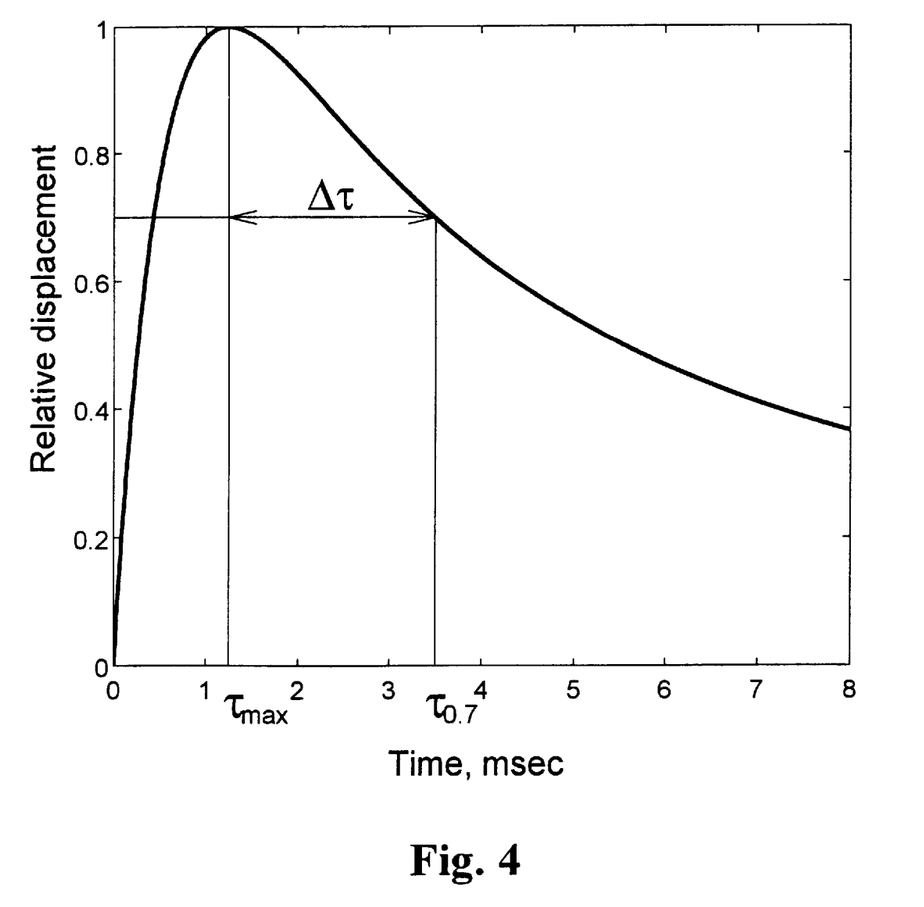
FIG. 4 is a plot at relative axial displacement of the focal point of the acoustic source.
Figure 5:
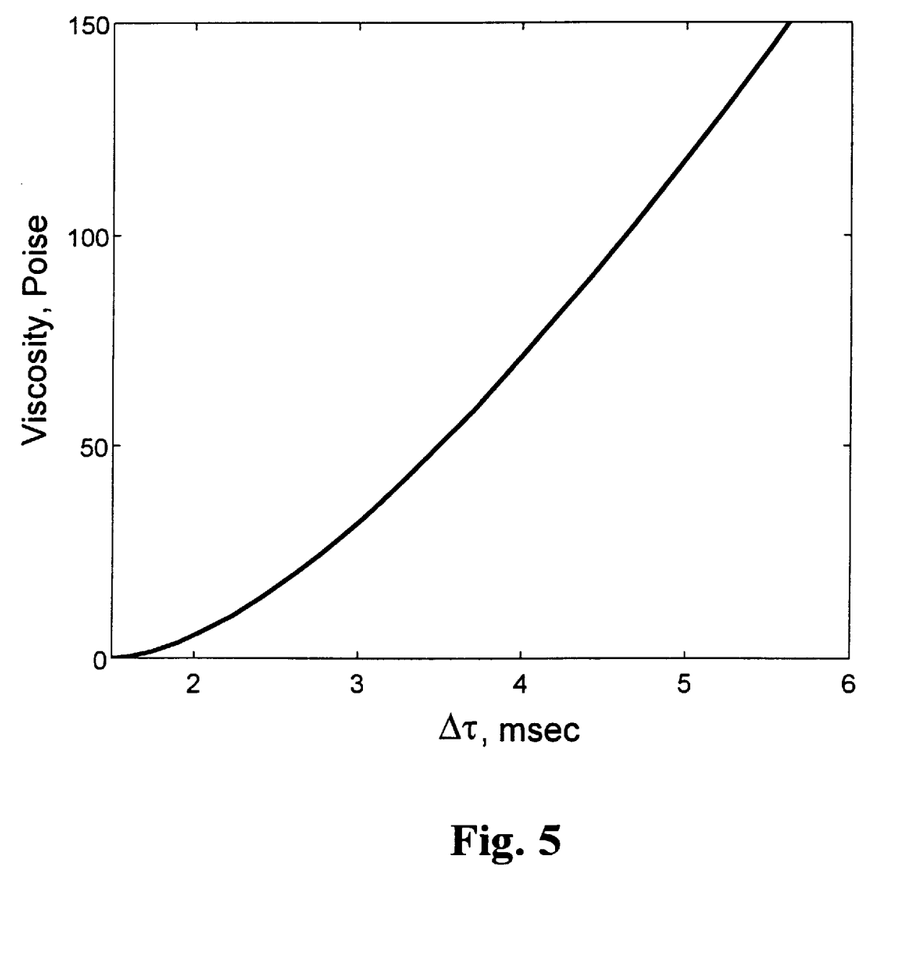
FIG. 5 is a calibration curve for evaluating dynamic viscosity of tissue from the measurement of the time required to get a 30% decrease of the displacement from its maximum value.

From FIG. 3, various methods of measurement of the tissue viscoelastic properties can be suggested. The first method is based on the measurement of the shear displacement on the beam axis in the focal region. The measurement in the single focal point has advantage that the shear displacement are largest at this point. In addition, the displacement estimation at one single point is the simplest and can be more convenient for technical implementations. As it was discussed above, temporal characteristic of the shear displacement in the focal region contain information on shear elasticity as well as dynamic shear viscosity of the tissue. The measurements of the time required for the displacement to reach the maximum at the focal point can be used for shear modulus estimation: $G=\rho(a/\tau_{max})^2$, and the rate of the displacement decrease depends on the tissue viscosity (FIG. 4). The time $\Delta\tau$ needed to decrease the displacement to the certain chosen level (this level in the FIG. 4 is chosen as 0.7 from the maximum) can be used for evaluating the dynamic shear viscosity of the tissue. FIG. 5 shows calculated dependence of the viscosity on the value of $\Delta\tau$. Such a calibration curve may be used for evaluating tissue viscosity from the temporal characteristic of the shear displacement in the focal region. The value of shear elasticity modulus of the tissue can be also calculated from the value of the maximum axial displacement in the focal point. The maximum displacement is inversely proportional to the shear elasticity modulus. In other words, the maximum displacement in a brain tissue having small shear elasticity modulus will be larger compared to the muscle tissue, for example. Therefore, it is possible to compare shear moduli of various tissues and to estimate their absolute values by measuring shear displacement $s_x$ in the focal point in the standard controlled conditions.

Figure 6:
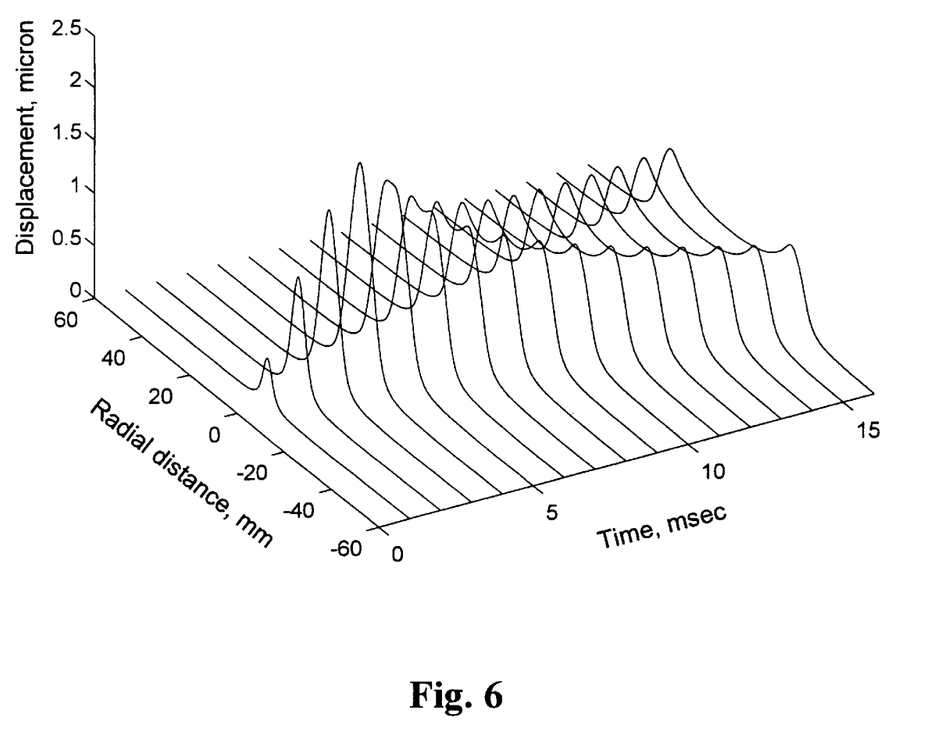
FIG. 6 is a representation of the temporal changes of the shear wave profile in the radial direction across the focal region of the focused acoustic source.
Figure 7:
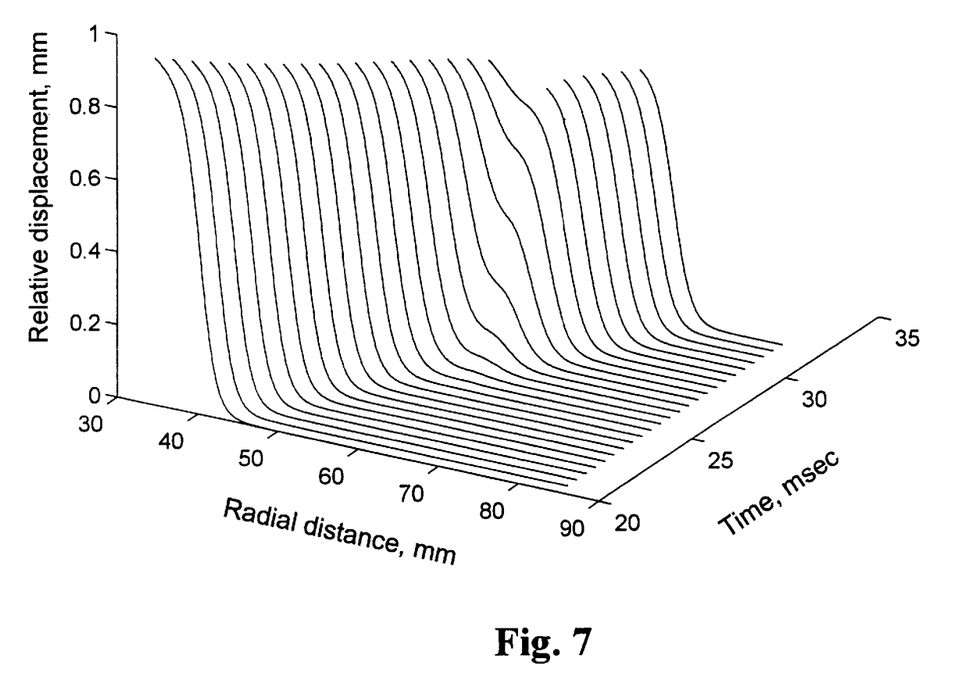
FIG. 7 illustrates propagation of a shear wave front in a tissue with a small hard inclusion.

Another method of shear modulus estimation is based on the measurement of a shear wave propagation parameters and changes of the wave front position. FIG. 6 shows profiles of the shear wave propagating radially from the focal point, calculated for the different time intervals from the generation of the wave. The same data as in FIG. 3 has been used for the calculation. Estimation of time needed for the wave front to propagate from one point to another, and the distance between these two points provides the shear wave speed $c_t$, and, consequently, shear modulus G. Attenuation of the propagating wave depends partly on the shear viscosity of the tissue. FIG. 7 shows propagation of the shear wave front through a region of the tissue containing a small hard inclusion 2 mm in diameter. Lines 205a–205d show the change in relative displacement due to the inclusion. The wave travels slower through the inclusion resulting in lower relative displacement over time than a wave traveling in normal tissue.

Figure 8:
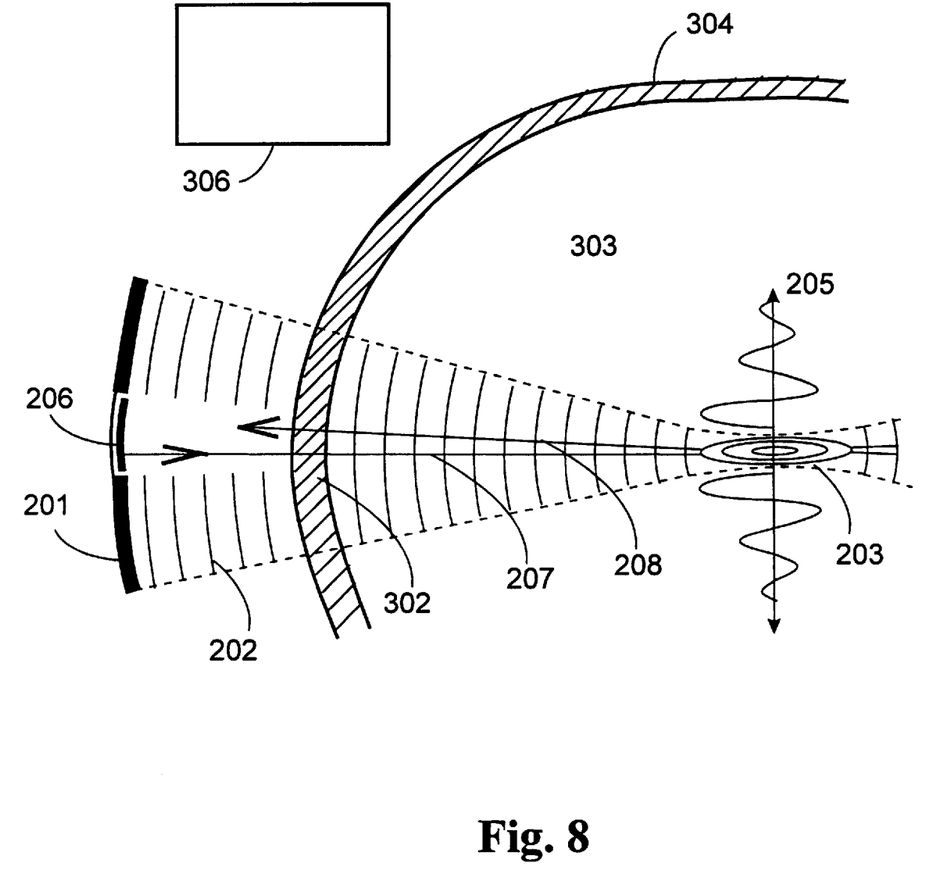
FIG. 8 is a schematic diagram of a shear wave elasticity imaging device for assessment of brain tissue.

The above described embodiments of devices for shear wave elasticity imaging can be used for elasticity imaging of the brain through an intact skull. FIG. 8 illustrates use of shear wave elasticity imaging device 300 for imaging brain tissue 303 through intact skull 304. Focused acoustic source 201 transmits focused pulse 202 through temporal bone 302 of skull 304. The use of focusing of ultrasound through an intact skull has been realized in a number of systems for ultrasonic therapy or diagnosis of brain. See, for example, J.-L. Thomas and M. A. Fink, *Ultrasonic Beam Focusing Throuah Tissue Inhomogeneities With a Time Reversal Mirror: Application to Transskull Therapy*. IEEE Transactions on Ultrasonics, Ferroelectrics, and Frequency Control, Vol. 43, No. 6, 1122–1129 (1966). Alternatively, MRI detector 306 can be used for detecting shear wave propagation parameters.

Detection of shear wave propagation parameters in brain tissue provides efficient descriptors for assessment of the mechanical state of the brain. The descriptors can include, for example, the amplitude of shear motion of the brain shear modulus. The application of shear wave elasticity imaging to the brain is advantageous in comparison to the application of SWEI for other types of tissue since the amplitude of the shear motion is inversely proportional to shear modulus of tissue and the brain shear modulus is over a magnitude less than the shear modulus for other types of tissue. The use of SWEI also provides a method for assessing through the intact skull such abnormalities as brain tumors, the extent of brain hemorrhage, the presence of intracranial edema, hematomas, or other mechanical damage to brain tissue. Many head injuries result in changes of mechanical properties of brain tissue, abnormal accumulation of fluid in intracranial vault, and/or changes in hemodynamics. The tissue of brain tumors is usually much harder than normal brain tissue and the application of SWEI to brain tissue provides a direct evaluation of brain tissue hardness through the intact skull in order to assess the pathological process. Application of SWEI to brain tissue can also be used as a method for detection and assessment of brain edema which can develop after head trauma or of insufficient oxygen supply to the brain. Personnel that use diving suits, submarine armor, altitude suit, etc., are exposed to the danger of brain edema resulting from failure of oxygen supply systems.

Figure 9:
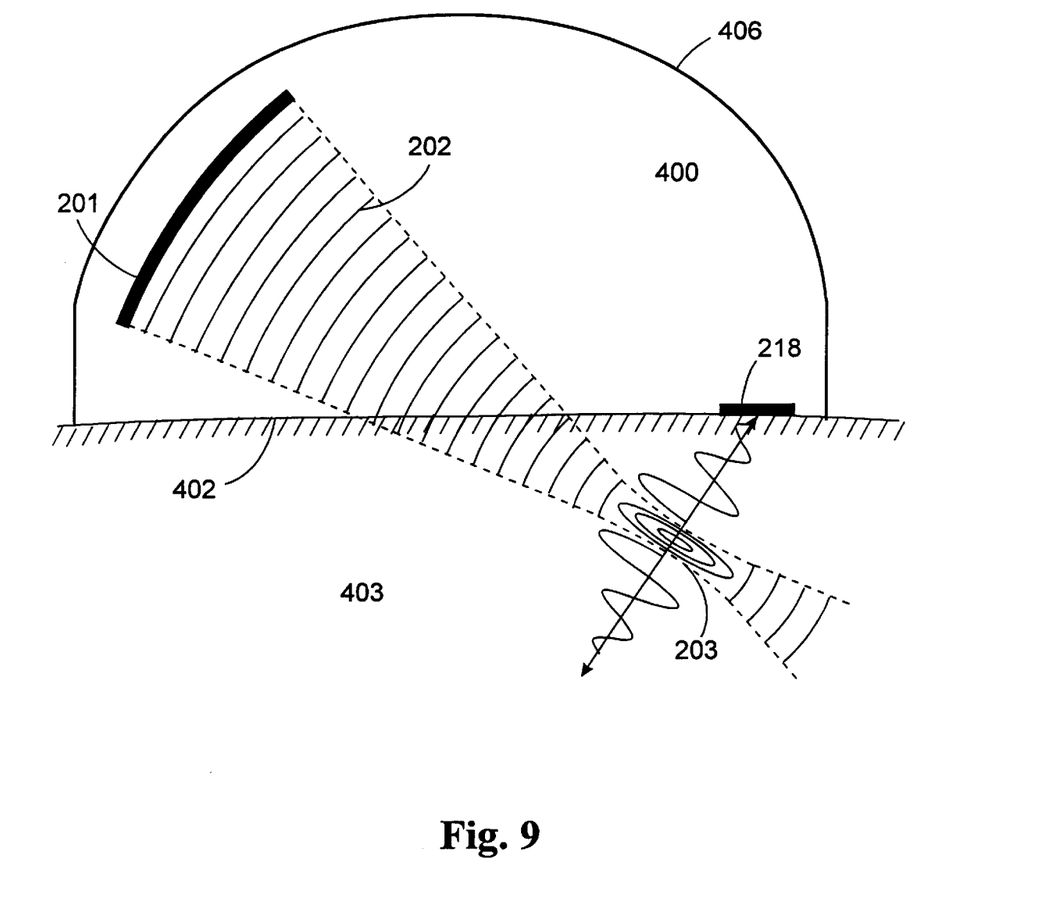
FIG. 9 is a schematic diagram of shear wave elasticity imaging device for assessment of muscle tissue.

The above described embodiments of devices for shear wave elasticity imaging can be used for evaluating the biomechanical state of muscle. FIG. 9 illustrates placement of shear elasticity imaging device 400 adjacent tissue surface 402 of muscle 403. Shear wave elasticity imaging device for assessment of mehcanical properties of muscle 400 can be similar to the embodiments shown in FIGS. 1–2. A device casing 406 of the probe of the device enclose focused acoustic source 201 and low frequency shear wave detector 218 400. Detection of shear wave propagation parameters of skeletal muscle provides information related to the muscle physiological activity and pathology. It can be used for muscle assessment in clinic and sport applications complementary to other methods of muscle examination, for example, normal muscle testing and electromyography. The parameters of the focused acoustic pulse are chosen such that the frequency of shear wave and the distance from focal region to tissue surface provide a detectable fraction of the shear wave energy to reach tissue surface. The measurements of muscle 403 can be made continuously in time and property calculator can continuously evaluate and display the measurement to monitor changes in the biomechanical state of muscle over time under varying conditions, such as exercise.

The data obtained by application of SWEI for assessment of skeletal muscle conditions in diagnostic and rehabilitation medicine can be used in biofeedback devices or in optimization exercise protocols in sport. The data can be used for prevention of musculotendinous injuries in sport, if it is used to control changes occurred in muscle in the course of warming up.

Evaluation of muscle tissue mechanical properties, such as the shear elasticity modulus and viscosity provide an indication of muscle function. The shear elasticity modulus provides an indication of muscle firmness. The shear elasticity modulus and the viscosity characterize the contraction and relaxation states of the muscle and are its most functionally relevant biomechanical parameters. The shear elasticity modulus is characteristic of both muscle tone and voluntary muscle contraction. Changes in muscle tone which occurs in many neuromuscular diseases (such as, for example, spastic paralysis, flaccid paralysis) can be determined by assessing the shear elasticity modulus. Muscle tone can also reflect the general conditions of the musculature, for example, immobilization of a body segment is accompanied by the loss of tone. Muscle firmness during exercise can be evaluated by determining the shear elasticity modulus. It is known that there are strong changes of the muscle firmness during contraction and relaxation processes. Typically, a voluntary muscle contraction is accompanied by a 515 fold increase in the shear elasticity modulus.

Evaluation of the dynamic viscosity of the muscle from propagating shear waves characterized the time dependence of the force/displacement relationship. Also, muscle viscosity can reflect other body conditions. For example, muscle viscosity depends on the blood content in the muscle and, therefore, can reflect cardiovascular processes accompanying muscular activity. The muscle viscosity can also reflect myoplasm or extracellular fluid viscosity. The viscosity of fluids affects velocity of muscle contraction and lowering the viscosity can be one of the factors determining the effectiveness of warm up on muscle performance.

Measurements of the viscoelastic properties can be used for the prevention of musculotendinous injuries incurred in sports. Muscle injury prevention is advocated by coaches and trainers because these injuries have a high incidence of recurrence. It is known that warm-up and stretching or warming up can result in muscle injury. However, the use of SWEI to characterize quantitatively the relaxed state of the muscle can aid in diminishing musculotendinous injuries due to improper warm up. Elasticity and viscosity of muscle vary over one order of magnitude during contraction and relaxation processes. Accordingly, the mechanical characteristics of muscle can be used as feedback parameters in optimizing exercise protocols. The determination of quantitative characterization of the contracted state of muscle by SWEI can be used to evaluate the efficacy of the contractile system and analyze the dependence of developed maximum force on the mode and time of training of an athlete. For example, to achieve a desired level in the physical ability of the body, or to reach the top performance in a given type of sport, a specific training protocol can be developed aimed at achieving a certain peak value of shear elastic modulus and/or the rate of the increase of modulus during a particular phase of an exercise. Measurement of the viscoelastic properties of muscle can be used in tailoring training system to varying personal objectives. For example, objective as "keeping the body in good shape", developing muscle, reaching the top muscular stresses with minimum risk of injury, producing the greater or faster contraction speed, etc., require a different target mechanical state of muscle. The above described SWEI device can be used to enable one to adjust the workload to the desired objective and corresponding target state of the muscle.

Although certain presently preferred embodiments of the present invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

We claim:

1. A method for determining the elasticity of tissue, comprising the steps of:

(a) remotely generating shear waves in the tissue using radiation force of a focused acoustic wave transmitted to a focal region of a focused acoustic source;

(b) detecting shear waves generated in the tissue;

(c) determining at least one propagation parameter of the shear waves in the tissue selected from the group of parameters consisting of shear wave velocity, shear wave attenuation coefficient, amplitude and velocity of shear displacement of tissue particles in the propagating shear wave; spatial and temporal dependencies of said amplitude and velocity of shear displacement of tissue particles; and (d) calculating, based on the results of step (c), at least one mechanical parameter of tissue selected from the group of parameters consisting of shear elasticity modulus, Young's modulus, dynamic shear viscosity, and mechanical impedance of the of tissue.

2. The method of claim 1, wherein said focused acoustic wave is a single acoustic pulse with duration in the range $10^{-2}$ to $10^{-9}$ seconds.

3. A method for determining the elasticity of muscle tissue, comprising the steps of:

(a) remotely generating shear waves in the muscle tissue using a focused acoustic wave;

(b) detecting shear waves generated in the muscle tissue;

(c) determining at least one propagation parameter of the shear waves in the muscle tissue selected from the group of parameters consisting of shear wave velocity, shear wave attenuation coefficient, amplitude and velocity of shear displacement of muscle tissue particles in the propagating shear wave; spatial and temporal dependencies of said amplitude and velocity of shear displacement of muscle tissue particles; and (d) calculating, based on the results of step (c), at least one mechanical parameter of the muscle tissue selected from the group of parameters consisting of shear elasticity modulus, Young's modulus, dynamic shear viscosity, and mechanical impedance of the muscle of the tissue.

4. The method of claim 3 wherein said focused acoustic wave is an amplitude modulated focused ultrasound wave.

5. The method of claim 3 wherein said focused acoustic wave is a single acoustic pulse.

6. The method of claim 5 wherein said single acoustic pulse has duration in the range of $10^{-2}$ to $10^{-9}$.

7. A method for determining the elasticity of brain tissue, comprising the steps of:

(a) remotely generating shear waves in the brain tissue using a focused acoustic pulse;

(b) detecting shear waves generated in the tissue;

(c) determining at least one propagation parameter of the shear waves in the brain tissue selected from the group of parameters consisting of shear wave velocity, shear wave attenuation coefficient, amplitude and velocity of shear displacement of brain tissue particles in the propagating shear wave; spatial and temporal dependencies of said amplitude and velocity of shear displacement of brain tissue particles; and (d) calculating, based on the results of step (c), at least one mechanical parameter of the brain tissue selected from the group of parameters consisting of shear elasticity modulus, Young's modulus, dynamic shear viscosity, and mechanical impedance of the of tissue.

8. The method of claim 7 wherein step (a) comprises the further step of focusing the acoustic wave at different locations in the tissue so as to generate the shear waves in the different locations in the tissue; and wherein the method comprises the further steps of:

repeating steps (b), (c) and (d) for each focused acoustic wave focused at said different locations in the tissue, and displaying the calculated values of dynamic shear viscosity and shear elasticity modulus as a function of the coordinates of said different locations in the tissue.

9. The method of claim 8 wherein said focused acoustic wave is a single acoustic pulse.

10. A device for determining elasticity of tissue, comprising:

transmitting means for transmitting a focused acoustic wave to a focal region so as to induce a shear wave in the tissue at said focal region;

detecting means for detecting the shear wave induced in the tissue at said focal region;

means for determining at least one propagation parameter of the shear waves in the tissue selected from the group of parameters consisting of shear wave velocity, shear wave attenuation coefficient, amplitude and velocity of shear displacement of tissue particles in the propagating shear wave; spatial and temporal dependencies of said amplitude and velocity of shear displacement of tissue particles; and calculating means for evaluating at least one mechanical parameter of tissue selected from the group of parameters consisting of shear elasticity modulus, Young's modulus, dynamic shear viscosity, and mechanical impedance of the of tissue.

11. The device of claim 10, wherein said transmitting means comprises an electrohydraulic acoustic transducer.

12. The device of claim 10, wherein said transmitting means comprises an optoacoustic source.

13. The device of claim 10, wherein said detecting means is a magnetic resonance imaging device.

14. The device of claim 10, wherein said detecting means is an interrogating ultrasonic transducer.

15. The device of claim 10, wherein said detecting means are electromagnetic waves induced by the shear motion of the tissue at said focal region.

16. The device of claim 10 where said detecting means is low frequency shear wave detector.

17. A device for determining elasticity of muscle tissue, comprising:

transmitting means for transmitting a focused acoustic wave to a focal region so as to induce a shear wave in the muscle tissue at said focal region;

detecting means for detecting the shear wave induced in the muscle tissue at said focal region;

means for determining at least one propagation parameter of the shear waves in the muscle tissue selected from the group of parameters consisting of shear wave velocity, shear wave attenuation coefficient, amplitude and velocity of shear displacement of muscle tissue particles in the propagating shear wave; spatial and temporal dependencies of said amplitude and velocity of shear displacement of muscle tissue particles; and calculating means for evaluating at least one mechanical parameter of muscle tissue selected from the group of parameters consisting of shear elasticity modulus, Young's modulus, dynamic shear viscosity, and mechanical impedance of the of muscle tissue.

18. The device of claim 17, wherein said detecting means is an interrogating ultrasonic transducer.

19. The device of claim 17, wherein said transmitting means transmits a focused acoustic wave through intact skull bone.

20. A device for determining elasticity of brain tissue, comprising:

transmitting means for transmitting a focused acoustic wave to a focal region so as to induce a shear wave in the brain tissue at said focal region;

detecting means for detecting the shear wave induced in the brain tissue at said focal region;

means for determining at least one propagation parameter of the shear waves in the brain tissue selected from the group of parameters consisting of shear wave velocity, shear wave attenuation coefficient, amplitude and velocity of shear displacement of brain tissue particles in the propagating shear wave; spatial and temporal dependencies of said amplitude and velocity of shear displacement of brain tissue particles; and calculating means for evaluating at least one mechanical parameter of brain tissue selected from the group of parameters consisting of shear elasticity modulus, Young's modulus, dynamic shear viscosity, and mechanical impedance of the of brain tissue.

21. The device of claim 20, wherein said detecting means is a magnetic resonance imaging device.

22. The device of claim 21, wherein said skull bone comprises temporal bone.

23. The device of claim 20 wherein said focused acoustic wave is a single acoustic pulse.

* * * * *